United States Patent

Davison et al.

[11] Patent Number: 6,062,212
[45] Date of Patent: *May 16, 2000

[54] DISPENSING APPARATUS

[75] Inventors: John Robin Davison; Paul Barnes, both of King's Lynn, United Kingdom; Geoffrey Brace, Cary, N.C.

[73] Assignee: Bespak Plc, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/392,978

[22] PCT Filed: Oct. 25, 1993

[86] PCT No.: PCT/GB93/02194

§ 371 Date: Apr. 11, 1995

§ 102(e) Date: Apr. 11, 1995

[87] PCT Pub. No.: WO94/09912

PCT Pub. Date: May 11, 1994

[30] Foreign Application Priority Data

Nov. 4, 1992 [GB] United Kingdom ............... 9223120

[51] Int. Cl.[7] .................................................. A61M 11/00
[52] U.S. Cl. ................................ 128/200.16; 128/200.14; 239/102.2
[58] Field of Search ..................... 128/200.14, 200.16, 128/200.17, 200.18, 200.21, 200.23, 203.12, 203.16, 205.15, 203.15; 239/102.2

[56] References Cited

U.S. PATENT DOCUMENTS

| 3,790,079 | 2/1974 | Berglund et al. |
|---|---|---|
| 3,806,100 | 4/1974 | Cornett, III et al. ............... 128/200.16 |
| 3,970,250 | 7/1976 | Drews ................... 128/200.16 |
| 4,465,234 | 8/1984 | Maehara et al. ..................... 239/102 |
| 4,570,630 | 2/1986 | Elliot et al. ......................... 128/203.15 |
| 4,877,989 | 10/1989 | Drews et al. ........................ 239/102.2 |
| 4,940,051 | 7/1990 | Lanleinen ........................... 128/203.15 |
| 4,962,868 | 10/1990 | Borchard ........................... 128/200.14 |
| 5,152,456 | 10/1992 | Ross et al. ......................... 128/200.16 |
| 5,297,734 | 3/1994 | Toda ................................... 239/102.2 |
| 5,586,550 | 12/1996 | Ivri et al. ........................... 128/200.16 |

FOREIGN PATENT DOCUMENTS

| 0084458 | 7/1983 | European Pat. Off. ........... 239/102.2 |
|---|---|---|
| 0156409 | 10/1985 | European Pat. Off. . |
| 2177623 | 1/1987 | United Kingdom ............... 239/102.2 |
| 2240494 | 8/1991 | United Kingdom . |
| 2265845 | 10/1993 | United Kingdom ............... 239/102.2 |
| 9106334 | 5/1991 | WIPO .............................. 128/200.14 |
| 8442091 | 8/1991 | WIPO .............................. 128/203.12 |
| 9310910 | 6/1993 | WIPO .............................. 239/102.2 |

*Primary Examiner*—John G. Weiss
*Assistant Examiner*—V. Srivastava
*Attorney, Agent, or Firm*—Smith, Gambrell & Russell, LLP

[57] ABSTRACT

A dispensing apparatus which defines an outlet through which a metered dose of liquid from a reservoir is dispersed as an atomized spray. A droplet of liquid is metered onto a perforate membrane which is vibrated by way of a piezo-electric transducer such that atomized droplets are dispensed through the holes formed in the membrane. At each actuation of a delivery device, which provides the metered quantity of liquid, the transducer is actuated so as to vibrate the membrane for a period greater than the dispensing period required for the droplet to be dispensed. The apparatus is particularly suitable for dispensing pharmaceutical preparations.

31 Claims, 5 Drawing Sheets

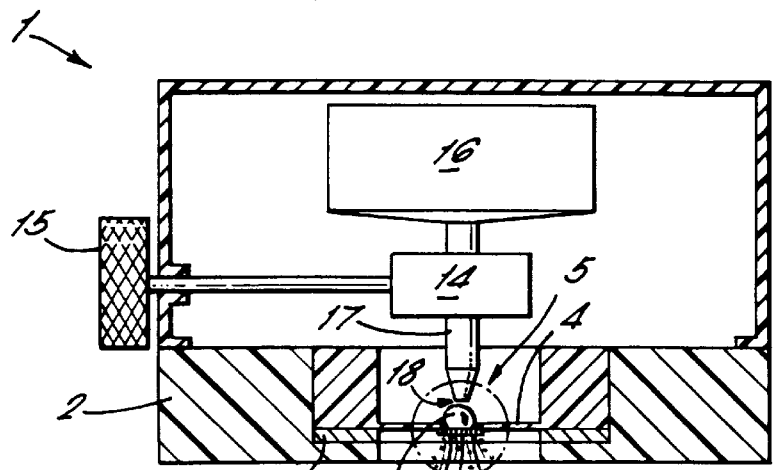
FIG. 1.
FIG. 1A.
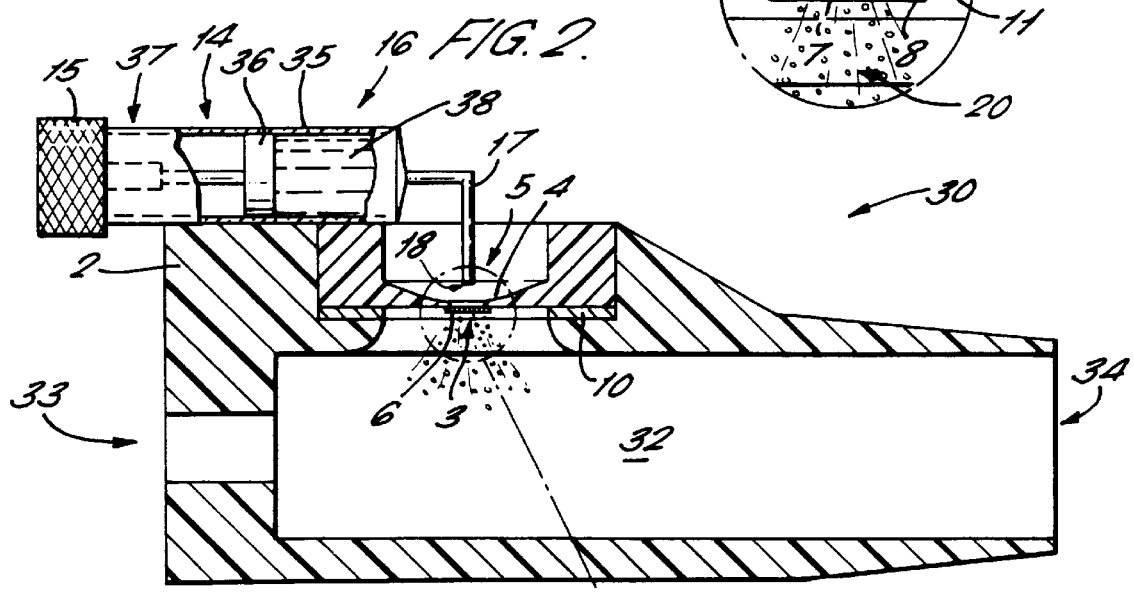
FIG. 2.
FIG. 2A.

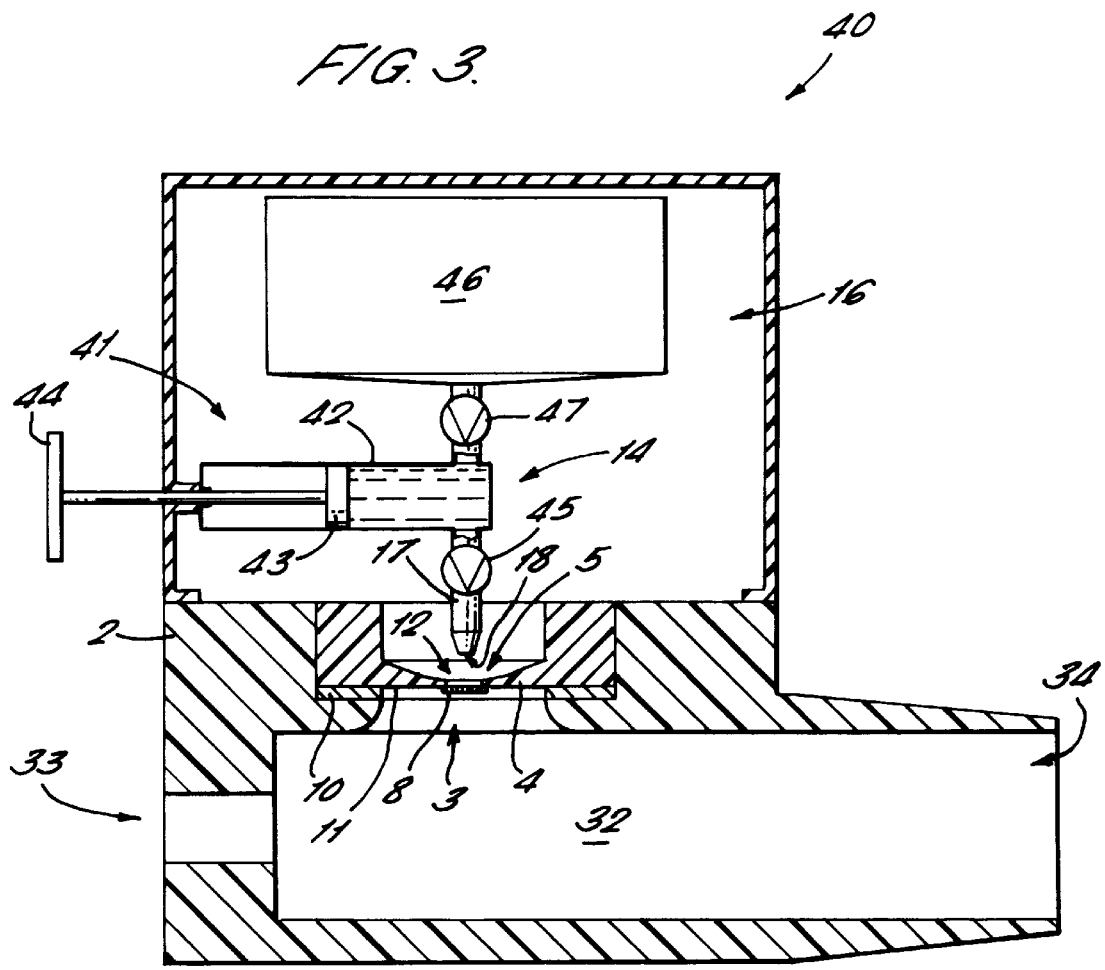

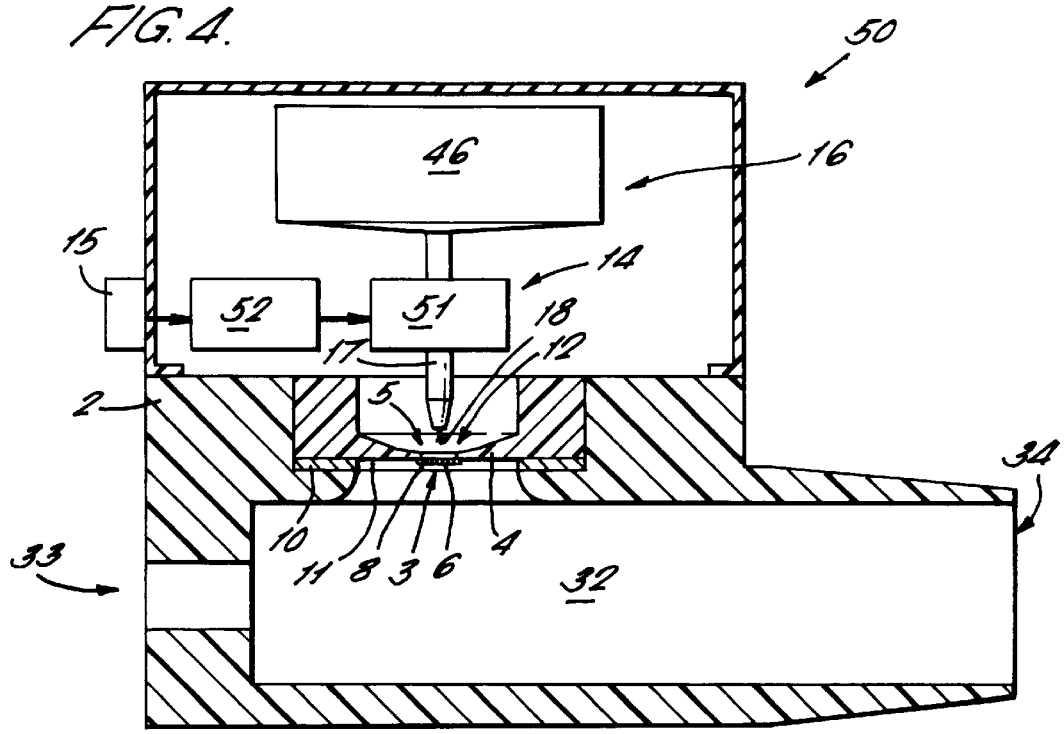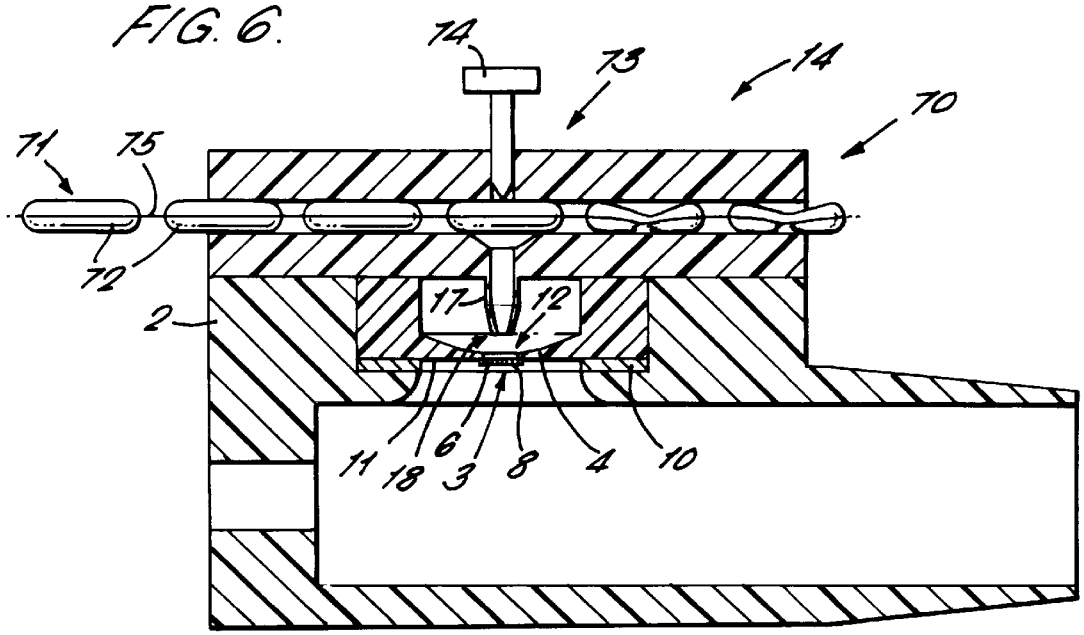

DISPENSING APPARATUS

FIELD OF THE INVENTION

This invention relates to dispensing apparatus for dispensing liquid as an atomised mist and in particular but not exclusively for dispensing medicaments for inhalation therapy.

BACKGROUND

It is known from GB-2240494A to provide dispensing apparatus in which a perforate membrane is vibrated such that liquid in contact with a rear face of the membrane is dispensed from a front face of the membrane as an atomised mist or spray. It is proposed that in the disclosed apparatus a predetermined dose is delivered by operation of a control circuit which regulates the dispensing period during which the membrane is vibrated, the supply of liquid being contained in a chamber of which the membrane constitutes a front wall.

A disadvantage of such an arrangement is that when not in use the liquid within the chamber is open to air through holes in the perforate membrane and may thereby be subject to evaporative losses or become bacteriologically contaminated or otherwise degraded.

A further disadvantage of such an arrangement is that variation in the rate at which liquid is dispensed through the membrane as a mist will result in variation in the total quantity delivered during the dispensing period.

SUMMARY OF THE INVENTION

According to the present invention there is disclosed dispensing apparatus comprising a housing defining a dispensing outlet, a perforate membrane having a front face exposed at the outlet and a rear face contacted in use by liquid to be dispensed, vibrating means connected to the housing and operable to vibrate the membrane to dispense droplets of the liquid through the membrane, liquid supply means connected to the housing and delivery means operable at successive actuations of the delivery means to deliver a respective metered quantity of the liquid from the liquid supply means into contact with the rear face of the membrane whereby in use a metered quantity of liquid is dispensible at the outlet by operation of the vibrating means for an operating period greater than the dispensing period required for the metered quantity to be dispensed through the membrane.

An advantage of such apparatus is that it facilitates the dispensing of all of the liquid coming into contact with the rear face of the membrane as a single dose. It is thereby possible to avoid contact between liquid and ambient air during periods of non-use between successive actuations. For pharmaceutical preparations this is particularly important since it may obviate the need for the use of preservatives in the liquid and avoids evaporative losses.

The liquid supply means conveniently comprises a pipette and the delivery means comprises a piston movably mounted in the pipette to displace, liquid therefrom and indexing means operable to move the piston at successive actuations through a respective distance to thereby displace a metered quantity of liquid.

Alternatively the liquid supply means may comprise a reservoir containing liquid and the delivery means may comprise a metering pump connected to the reservoir, the metering pump comprising a cylinder defining a chamber and a piston reciprocatably mounted in the cylinder to displace a metered volume of liquid from the chamber at each actuating stroke.

Alternatively the delivery means may comprise an electrically driven pump operable to deliver a flow of liquid and control means operable to turn the pump on and to turn the pump off after delivery of the metered volume of liquid.

In an alternative apparatus the liquid supply means comprises a pressurised dispensing container within which a supply of liquid is maintained under pressure and the delivery means comprises a metering valve operable to release from the container a metered volume of the liquid.

In a further alternative apparatus the liquid supply means comprises a plurality of cells each containing a metered volume of liquid and the delivery means comprises a dispensing station operable to release at each actuation thereof the contents of a respective cell.

Preferably the housing comprises an annular member connected peripherally to the vibrating means and defining a central aperture overlaid by the membrane.

Preferably the annular member comprises an upper surface which is concave so as to be downwardly sloping in a radially inward direction when the apparatus is held in use in a preferred operating orientation.

Advantageously the tipper surface of the annular member is formed of a liquid repellant material. A liquid droplet deposited on the tipper surface is thereby encouraged to move radially inwardly into contact with the membrane.

Conveniently the annular member comprises a radially innermost surface portion defining the aperture and co-operating with the membrane to define a well for receiving in use a droplet of liquid to be dispensed.

The housing may define a duct communicating between an air inlet and an outlet port, the dispensing outlet being located in the duct intermediate the air inlet and the outlet port such that the front face of the membrane is exposed to air within the duct.

The outlet port may be an inhalation port for oral or nasal use.

Such an arrangement is useful in the administration of inhaled pharmaceutical liquid products where it is required for an atomised spray of liquid to be entrained in an inhaled air flow passing through the duct.

Apparatus in accordance with the present invention may be provided with an air impeller connected to the housing so as to be operable to create a flow of air through the duct from the air inlet to the outlet port.

Such an arrangement may be used for dispensing cosmetics and perfumes. A further application of such an arrangement is opthalmic use where an opthalmic preparation can be used to generate an atraumatic mist which is administered to the user's eye by means of an eye cup provided in the housing so as to communicate with the duct.

BRIEF DESCRIPTION OF THE PREFERRED EMBODIMENTS

Particular embodiments of the present invention will now be described by way of example only and with reference to the accompanying drawings of which:

FIG. 1 is a schematic sectioned elevation of a first apparatus in accordance with the present invention;

FIG. 1A is an enlarged view of the circled area in FIG. 1;

FIG. 2 is a schematic sectioned elevation of an alternative apparatus having a pipette with an indexing mechanism;

FIG. 2A is an enlarged view of the circled area in FIG. 2;

FIG. 3 is a schematic sectioned elevation of a further alternative apparatus having a metering pump;

FIG. 4 is a schematic sectioned elevation of a further alternative apparatus having an electrically driven pump;

FIG. 6 is a schematic sectioned elevation of a further alternative apparatus in which the liquid supply means comprises a plurality of cells whose respective contents are released during successive actuations at a dispensing station;

DETAILED DESCRIPTION OF THE PREFERRED EMBODIMENTS OF THE INVENTION

Figure 5:
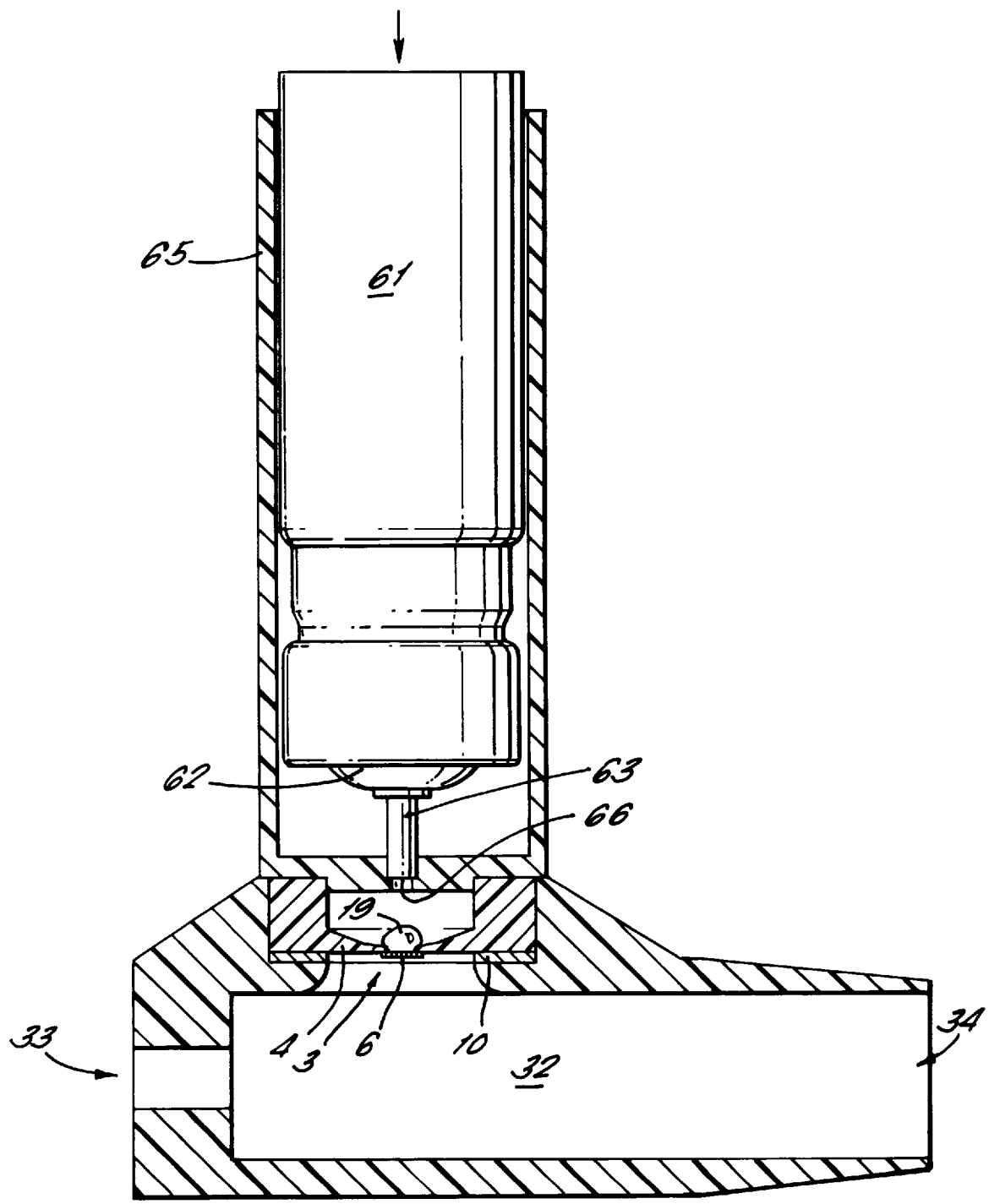
FIG. 5 is a schematic sectioned elevation of a further alternative apparatus having a pressurised dispensing container with a metering valve.

In FIG. 1 a first apparatus 1 has a housing 2 defining an outlet 3. The housing 2 includes an annular member 4 defining a central aperture 5 which is overlaid by a perforate membrane 6.

The membrane 6 is peripherally bonded to the annular member 4 so as to close the aperture 5 and defines an array of holes 7 of 3 microns diameter and 25 microns spacing.

The annular member 4 extends horizontally such that a front face 8 of the membrane 6 is downwardly oriented and a rear face 9 of the membrane is upwardly directed.

The annular member 4 extends radially with uniform thickness into contact with an annular piezoelectric transducer 10 which is connected to an oscillator circuit (not shown) operable to energise the transducer. The transducer 10 is arranged such that vibration is applied at right angles to the plane of the annular member 4 such that transverse acoustic waves are propagated radially inwardly of the annular member so as to excite the membrane 6 in an axial direction i.e. producing vertical movement of the membrane.

The membrane 6 is bonded to a lower surface 11 of the annular member 4 such that, because of the finite thickness of the member at the aperture 5, a shallow well 12 is defined in the aperture 5 above the membrane 6 and bounded radially by an inner vertical annular face 13 of the annular member 4.

A delivery means 14 is located within the housing 2 and is operable by means of an actuator 15 to deliver at each actuation a metered volume of liquid from a liquid supply means 16, the liquid being delivered through a delivery tube 17 to a delivery location 18 immediately adjacent and above the membrane 6.

A droplet of liquid 19 is shown located on top of the membrane 6 within the well 12 immediately following actuation of the delivery means 14 to dispense a metered volume of 20 microliters of liquid, the membrane being vibrated to produce an atomised spray 20 in the air surrounding the outlet 3.

In use, the membrane 6 is initially free from liquid and a metered volume is dispensed by actuation of the delivery means 14 such that a droplet of liquid is placed in the well 12. The vibrating means is then actuated and continues to vibrate the membrane 6 for an operating period determined by a timer (not shown).

The operating period is selected to be greater than the dispensing period required to dispense all of the liquid contained in the droplet 19 as an atomised spray or mist through the membrane holes 7.

Since in practice the dispensing period required to totally dispense a metered volume will vary from actuation to actuation, the operating period is selected to be sufficiently greater than the average dispensing period in order to accommodate such variation thereby ensuring that the quantity of liquid dispensed is independent of the rate at which the liquid flows through the membrane.

The vibrating means is then de-actuated until further use is required.

An alternative apparatus 30 shown in FIG. 2 will now be described using corresponding reference numerals to those of FIG. 1 where appropriate for corresponding elements.

The second apparatus 30 includes a housing 2 with an annular member 4 supporting a membrane 6 for vibration by actuation of a transducer 10. The annular member 4 has an upper surface 31 which is concave and downwardly sloping in a radially inward direction so that the aperture 5 is located at the lowest part of the surface 31 thereby assisting draining of any liquid on the upper surface 31 into the well 12.

The upper surface 31 is coated with a liquid repellant surface to assist this draining action and ensure that any droplet of liquid deposited on the upper surface finds its way into contact with the membrane 6.

The housing 2 defines a horizontally extending cylindrical duct 32 communicating between an air inlet 33 and an inhalation port 34 suitable for oral inhalation. The outlet 3 is located intermediate the inlet 33 and the inhalation port 34 so as to communicate with the duct 32, the membrane 6 having a front face 8 which is directly exposed to air within the duct 32.

The second apparatus 30 has a delivery means 14 comprising a pipette 35 within which a piston 36 is advanceable by means of an indexing mechanism 37 in discrete measured steps so as to displace metered volumes of liquid 38 from the pipette. A delivery tube 17 communicates between the pipette 35 and a delivery location 18 so as to dispense a metered quantity of the liquid into contact with the membrane 6 at each actuation of the indexing mechanist 37.

In use the indexing mechanism is actuated to deliver a drop into the well 12 and the vibrating means is then actuated. Vibration of the membrane 6 discharges a fine mist 20 of droplets into the duct 32 until such time as the liquid within the well is entirely consumed. The mist is entrained in an air flow within the duct when the user inhales air through the inhalation port 34 such that the liquid is orally administered for inhalation into the user's lungs.

A third apparatus 40 is shown in FIG. 3 and will now be described using corresponding reference numerals to those of preceding Figures where appropriate for corresponding elements.

The third apparatus 40 includes a housing 2, annular member 4 and duct 32 of the type described above with reference to the second apparatus 30 in FIG. 2. The third apparatus 40 differs in that the delivery means 14 is a manually actuated metering pump 41 which has a cylinder 42 receiving a piston 43 actuated by means of an actuator 44. At each actuation a single stroke of the piston 43 displaces from the cylinder 42 a metered quantity of liquid which flows through a one-way outlet valve 15 into delivery tube 17. The piston then returns to its rest position and the chamber is refilled for further operation. The cylinder 42 and piston 43 are shown schematically in FIG. 3 and not to scale, the appropriate stroke and metered volume in a practical arrangement being selected to dispense a drop of liquid at each actuation.

Liquid is supplied to the pump 41 from a reservoir 46 via an inlet valve 47, the reservoir being of sufficient capacity to contain a large number of metered volumes of liquid.

In use the metering pump 41 is actuated by manual depression of the actuator 44 and a single stroke of the piston 43 displaces a droplet of liquid on to the membrane 6 via the delivery tube 17.

Figure 7:
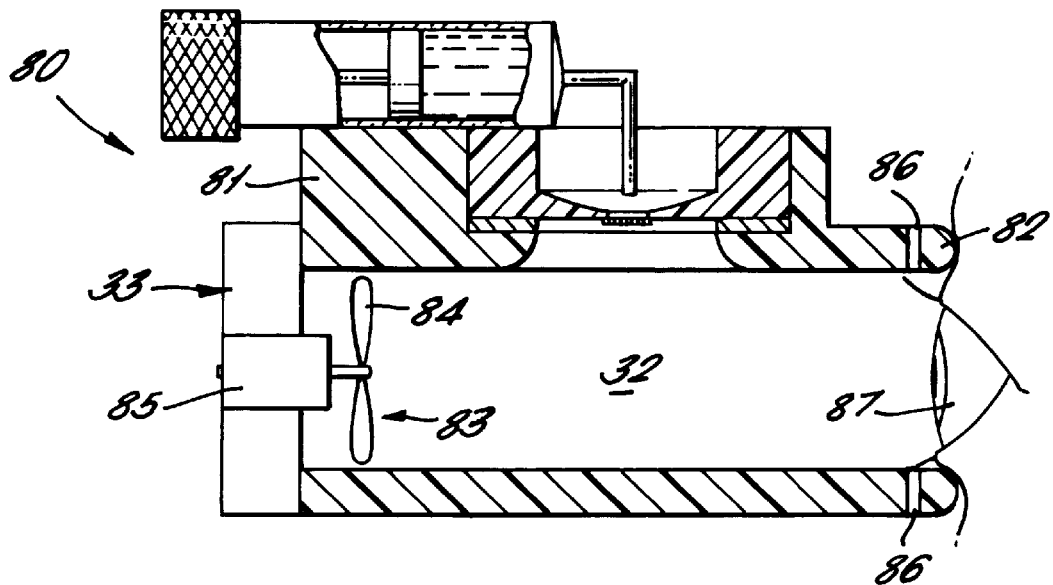
FIG. 7 is a schematic sectioned elevation of a further alternative apparatus for use in dispensing an opthalmic preparation.
Figure 8:
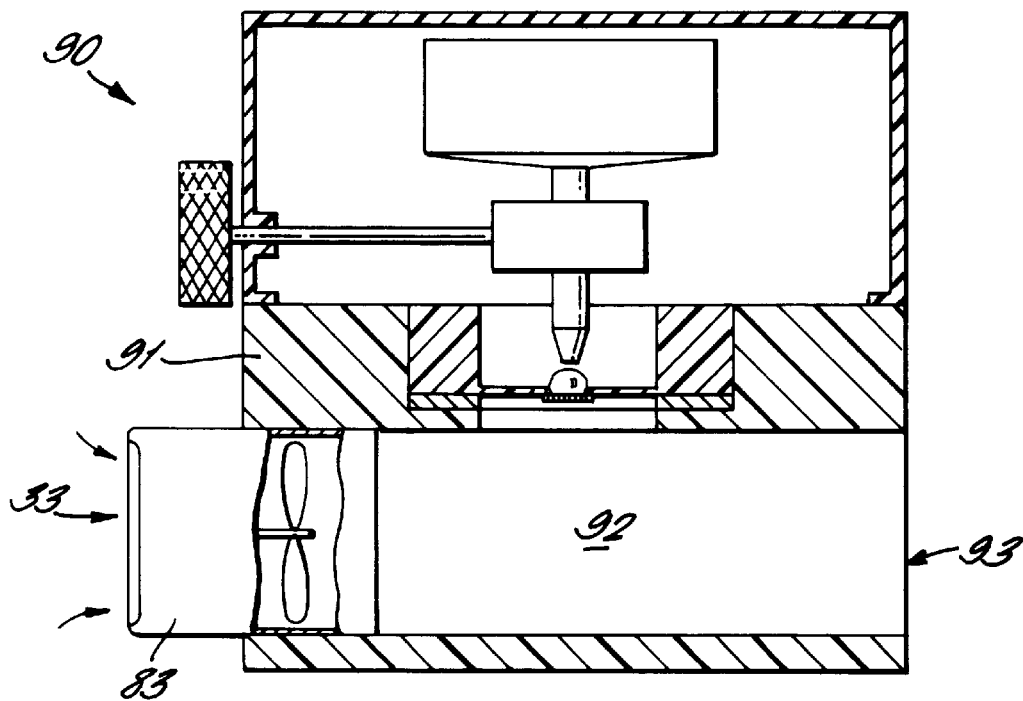
FIG. 8 is a schematic sectioned elevation of a further alternative apparatus having an air impeller for dispensing cosmetic preparations.

The transducer 10 is then actuated so as to vibrate the membrane and dispense atomised droplets into the duct 32 from where they are inhaled by the user via the inhalation port 34. After a time period sufficient for the droplet to be consumed the transducer 10 is de-actuated and the apparatus is ready for further use.

A fourth alternative apparatus 50 shown in FIG. 4 will now be described using corresponding reference numerals to those of preceding Figures where appropriate for corresponding elements.

The apparatus 50 is generally similar to the third apparatus 40 of FIG. 3 but includes an electrically operated pump 51 which is operable to deliver liquid from a reservoir 46 to a delivery location 18 when energised by a controller circuit 52.

The pump 51 is a peristaltic pump providing a continuous output flow when energised and the controller circuit 52 achieves delivery of a measured volume by controlling the duration for which pump 51 is energised.

Once a metered volume of liquid has been delivered on to the membrane 6 the operation of the apparatus 50 corresponds to that of the third apparatus 40 described above.

A fifth apparatus 60 shown in FIG. 5 will now be described using corresponding reference numerals to those of preceding Figures where appropriate for corresponding elements.

The fifth apparatus 60 includes a housing 2 with an annular member 4 supporting membrane 6 of the same general type as those described above with reference to FIGS. 2, 3 and 4. A quantity of liquid is contained within a pressurised dispensing container 61 of a type commonly utilised in aerosol dispensers. The container 61 has a metering valve 62 operable to dispense a metered volume of liquid through a tubular stem 63 in response to depression of the stem 63 relative to the container 61.

The stem 63 is received within a socket 64 fixed to the housing 2 and the container 61 is displaceable relative to a tubular sheath 65 extending upwardly of the housing so as to provide relative movement between the container and the stem 63 thereby enabling the metering valve 62 to be actuated by manual depression of the container 61 relative to the housing 2.

The socket 64 defines a delivery orifice 66 communciating with the stem 63 and through which the liquid is dispensed on to the membrane 6.

In use the membrane is vibrated by actuation of the transducer 10 for a period sufficient to totally atomise a droplet of liquid received within the well 12 so that a fine mist can be orally inhaled via the duct 32.

A sixth apparatus 70 is shown in FIG. 6 and will now be described using corresponding references to those of preceding Figures where appropriate for corresponding elements.

The sixth apparatus 70 includes a housing 2, an annular member 4 and a membrane 6 of the type disclosed with reference to FIGS. 2 to 5. A delivery means 14 comprises a liquid supply means 71 in which metered quantities of liquid are contained within individual cells 72. The cells 72 are fed in turn to a dispensing station 73 which is operable by depression of an actuator 74 to release the contents of a cell and conduct the contents of the cell via delivery tube 17 on to the membrane 6.

The cells 72 comprise gelatin capsules formed on a disposable strip 75 which is fed to the dispensing station 73 where the capsules are ruptured by action of the actuator 74 during each dispensing operation.

A seventh apparatus 80 is shown in FIG. 7 and will now be described using corresponding references to those of preceding Figures where appropriate for corresponding elements.

The seventh apparatus 80 is based on the second apparatus 30 of FIG. 2 but includes a modified housing 81 in which the inhalation port 34 of FIG. 2 is replaced by an eye cup 82 and air inlet 33 is provided with an air impeller 83.

The air impeller 83 consists of a fan 84 driven by an electric motor 85 so as to create a flow of air along duct 32 and air release holes 86 are provided adjacent to the eye cup 82 to allow the escape of air peripherally of the eye cup.

The seventh apparatus 80 is operable to dispense an aerosol mist into the duct 32 in the same manner as the second apparatus 30 of FIG. 2. The product dispensed as a liquid is an opthalmic preparation providing an atraumatic mist delivered to the user's eye 87 when engaged with the eye cup 82.

An eighth apparatus 90 is shown in FIG. 8 and will now be described using corresponding references to those of preceding Figures where appropriate for corresponding elements.

The eighth apparatus 90 is based on the first apparatus 1 of FIG. 1 but includes a modified housing 91 which defines a cylindrical duct into which the outlet 3 opens to release an atomised spray in use. The duct 92 has an outlet 93 through which air emerges when a flow of air through the duct 92 is created by an air impeller 83 located in the air inlet 33. The air impeller 83 comprises a fan 84 driven by an electric motor.

The eighth apparatus 90 is primarily intended for dispensing cosmetic preparations, perfumes and fragrances.

The apparatus shown in FIG. 1 may be used in applications other than for medical inhalation therapy such as to dispense cosmetic preparations including perfume.

The apparatus of FIGS. 2 to 6 is suitable for inhalation therapy and may in each case be modified to include an inhalation sensor in order to synchronise the release of droplets through the membrane with inhalation by the user. The inhalation port may be adapted for oral or nasal inhalation.

The fourth apparatus shown in FIG. 4 with reference to a peristaltic pump may alternatively use a piezoelectric micro pump of the type disclosed in EP-0398583A in which a diaphragm is reciprocated by action of a piezoelectric transducer.

The seventh apparatus 80 of FIG. 7 may alternatively be provided with a metering pump of the type disclosed with reference to FIG. 3 or FIG. 4 or alternatively may utilise the pressurised dispensing container 61 and metering valve 62 of the fifth apparatus shown in FIG. 5. Alternatively the liquid supply means 71 of FIG. 6 may be utilised in the seventh apparatus 80.

Similar comments apply to the eighth apparatus 90 where similarly alternative arrangements way be utilised to deliver a droplet on to the membrane 6.

The air impeller 83 utilised in FIGS. 7 and 8 may be replaced by an equivalent arrangement such as a mechanically driven fan or bellows arrangement.

The fifth apparatus 70 may alternatively be used with different types of package defining individual cells. For example a plastic, aluminium or laminated strip may be formed so as to define pockets each defining a cell containing a pre-measured quantity of liquid, each pocket being closed by a second strip of plastic, aluminium foil or a laminate. The liquid may then be released by piercing the pocket or by peeling off the second strip.

In the configuration shown in FIG. 6, individual metered quantities of liquid are placed in the packaging at the time of manufacture. Each dose is consumed at each actuation of the dispensing apparatus. This arrangement has the advantage of providing for different doses to be administered by the apparatus by providing a range of packaged doses of predetermined volume from which the required dose can be selected or prescribed as may be required.

The frequency vibration of the membrane described above with reference to each of the embodiments may be selected to any suitable value, preferably in the kilohertz to megahertz range.

The pressurised dispensing container of FIG. 5 may be of the conventional type in which an evaporable propellant is mixed with a liquid product or of an alternative type such as a container adapted to dispense under pressure from a compressed gas. The liquid product may be contained separately from the propellant liquid or gas within a collapsible bag or compartment.

We claim:

1. Dispensing apparatus comprising a housing defining a dispensing outlet, a perforate membrane having a front face exposed at the outlet and a rear face contacted in use by liquid to be dispensed, vibrating means connected to the housing and operable to vibrate the membrane to dispense droplets of the liquid through the membrane, liquid supply means connected to the housing and having an outlet valve, and delivery means operable at successive actuations of the delivery means to deliver a respective metered quantity of the liquid from the liquid supply means via the outlet valve into contact with the rear face of the membrane and means for operating the vibrating means for an operating period greater than a dispensing period required for the metered quantity to be dispensed though the membrane whereby in use all of the dispensed liquid is consumed prior to the next successive actuation of the delivery means, such that the liquid is isolated from the ambient air between successive actuations of the delivery means.

2. Dispensing apparatus as claimed in claim 1 wherein the liquid supply means comprises a reservoir containing liquid and the delivery means comprises a metering pump connected to the reservoir, the metering pump comprising a cylinder defining a chamber and a piston reciprocatably mounted in the cylinder to displace a metered volume of liquid from the chamber at each actuating stroke.

3. Dispensing apparatus as claimed in claim 1 wherein the liquid supply means comprises a pressurised dispensing container within which a supply of liquid is maintained under pressure and the delivery means comprises a metering valve constituting the outlet valve and operable to release from the container the metered quantity of liquid.

4. Dispensing apparatus as claimed in claim 1 wherein the housing comprises an annular member connected peripherally to the vibrating means and defining a central aperture overlaid by the membrane.

5. Dispensing apparatus as claimed in claim 4 wherein the annular member comprises an upper surface which is concave so as to be downwardly sloping in a radially inward direction when the apparatus is held in use in a preferred operating orientation.

6. Dispensing apparatus as claimed in claim 5 wherein the upper surface of the annular member is formed of a liquid repellant material.

7. Dispensing apparatus as claimed in claim 5 wherein the annular member comprises a radially innermost surface portion defining the aperture and co-operating with the membrane to define a well for receiving in use a droplet of liquid constituting the metered quantity of liquid to be dispensed.

8. Dispensing apparatus as claimed in claim 1 wherein the housing defines a duct communicating between an air inlet and an outlet port, the dispensing outlet being located in the duct intermediate the air inlet and the outlet port such that the front face of the membrane is exposed to air within the duct.

9. Dispensing apparatus as claimed in claim 8 wherein an air impeller is connected to the housing so as to be operable to create a flow of air through the duct from the air inlet to the outlet port.

10. Dispensing apparatus as claimed in claim 9 wherein the housing defines an eye cup communicating with the duct.

11. Dispensing apparatus as claimed in claim 8 wherein the outlet port comprises an inhalation port for oral or nasal use.

12. Dispensing apparatus as claimed in claim 1 wherein the means for operating the vibrating means comprises a timer connected to the vibrating means and operable to determine the operating period during which the vibrating means is actuated and wherein the operating period is selected to be greater than the dispensing period required for the metered quantity to be dispensed through the membrane.

13. A method of dispensing liquid as an atomised spray comprising the steps of delivering a metered quantity of liquid from a liquid supply means via an outlet valve into contact with a rear face of a perforate membrane vibrating the membrane such that liquid is dispensed through the membrane as an atomised spray, wherein the membrane is initially free from liquid and the liquid is isolated from the ambient air between successive deliveries of liquid and in that the membrane is vibrated for an operating period grater than a dispensing period required for the metered quantity to be fully dispensed.

14. Dispensing apparatus comprising a housing defining a dispensing outlet, a perforate membrane having a front face exposed at the outlet and a rear face contacted in use by liquid to be dispensed, vibrating means connected to the housing and operable to vibrate the membrane to dispense droplets of the liquid through the membrane, liquid supply means connected to the housing and delivery means operable at successive actuations of the delivery means to deliver a respective metered quantity of the liquid from the liquid supply means into contact with the rear face of the membrane whereby in use a metered quantity of liquid is dispensible as an atomised spray at the outlet by operation of the vibrating means for an operating period greater than a dispensing period required for the metered quantity to be dispensed through the membrane and wherein the liquid supply means comprises a plurality of cells each containing a metered volume of liquid and the delivery means comprises a dispensing station operable to release at each actuation thereof the contents of a respective cell.

15. Dispensing apparatus as recited in claim 1, wherein said delivery means delivers a droplet of liquid to said rear face of said perforate membrane and said droplet of liquid constitutes the metered quantity of liquid to be dispensed.

16. Dispensing apparatus as recited in claim 5, wherein said delivery means delivers a droplet of liquid to said rear face of said perforate membrane and said droplet of liquid constitutes the metered quantity of liquid to be dispensed.

17. The method of dispensing liquid as described in claim 13, wherein delivering a metered quantity of liquid to the rear face of said perforate membrane includes delivering a droplet of liquid to said rear face with said droplet constituting the metered quantity of liquid to be dispensed.

18. A dispensing apparatus comprising:
a sealed liquid supply container;
a delivery tube extending from said supply container and being in fluid communication with said supply container at a first end and having an outlet nozzle end at an opposite end;
a liquid drop reception device which includes a liquid drop reception well for receiving a liquid drop delivered by said delivery tube and which liquid drop reception well is at least partly defined by a perforated membrane, and said nozzle outlet and membrane being positioned such that a liquid drop derived from said sealed liquid supply container is positioned between the nozzle outlet and said membrane with the liquid drop attached to the membrane;
a housing structure that is configured so as to preclude environmental contact with the liquid except through perforations formed in said membrane, and the perforations in said membrane being dimensioned so as to create an atomized spray of liquid droplets upon vibration of said membrane.

19. Dispensing apparatus comprising a housing defining a dispensing outlet, a perforate membrane having a front face exposed to the outlet and a rear face contacted in use by liquid to be dispensed, vibrating means operable to vibrate the membrane to dispense droplets of the liquid through the membrane, liquid supply means supported by said housing and having an outlet valve, and delivery means operable at successive actuations of the delivery means to deliver a respective metered, single dose quantity of the liquid from a multi-dose supply liquid of the liquid supply means via the outlet valve into contact with the rear face of the membrane and said outlet valve of said liquid supply means and said delivery means being arranged so as to isolate the multi-dose supply of liquid of said liquid supply means from contact with contaminants between successive actuations of the liquid supply means, and said dispensing apparatus further comprising operating means for operating the vibrating means for an operating period greater than a dispensing period required for the metered quantity to be dispensed through the membrane whereby in use all of the dispensed liquid is consumed prior to the next successive actuation of the delivery means, such that the liquid of said liquid supply means is isolated from contaminants and there is avoided any dispensed liquid remaining on said membrane between the end of an operating period and the next successive actuation of the delivery means.

20. A dispensing device as recited in claim 19 wherein the operating period of said operating means is based on a time period set by a timer of said operating means.

21. A dispensing apparatus as recited in claim 18, wherein the perforations in said membrane are dimensioned so as to produce a fine mist of liquid droplets suitable for inhalation therapy and said sealed liquid supply container contains a pharmaceutical liquid.

22. A dispensing device as recited in claim 18, wherein said liquid drop reception device includes an annular support member extending about said membrane and having a peripheral section in contact with said housing.

23. A dispensing device as recited in claim 22, wherein said annular support member includes a converging section which has a thinnermost portion secured to said perforated membrane for centering the liquid drop on the membrane.

24. A dispensing device as recited in claim 18, further comprising a piezo electric vibrator for vibrating said perforated membrane with said piezo electric vibrator being supported by said housing.

25. A dispensing apparatus as recited in claim 18, further comprising a valve in line with said delivery tube which releases the one drop when open and seals off the supply container when closed.

26. A dispensing apparatus as recited in claim 18, further comprising means for vibrating said membrane and means for operating said vibrating means for an operating period which exceeds a period of time required for dispensing the drop received on said membrane at a vibration rate of said means for vibrating.

27. A dispensing device as recited in claim 18, wherein said sealed liquid container is flexible so as to be deformable and is sized so as to include a single dose of liquid such that when said liquid container is deformed in use all liquid contained therein is released to said delivery tube so as to be received by said perforated membrane.

28. A dispensing device as recited in claim 27, wherein said delivery tube converges in diameter with a larger inlet end and has an axis of elongation which is positioned so as to extend through said membrane.

29. A dispensing device as recited in claim 18, wherein said delivery tube is arranged vertically within said housing such that the liquid drop drops down into contact with a rear face of said membrane upon release from said delivery tube.

30. Dispensing apparatus comprising a housing defining a dispensing outlet, a perforate membrane having a front face exposed to the outlet and a rear face contacted in use by liquid to be dispensed, vibrating means connected to the housing and operable to vibrate the membrane to dispense droplets of the liquid through the membrane, liquid supply means connected to the housing and having an outlet valve, and delivery means operable at successive actuations of the delivery means to deliver a respective metered quantity of the liquid form the liquid supply means via the outlet valve into contact with the rear face of the membrane, and means for operating the vibrating means for an operating period greater than a dispensing period required for the metered quantity to be dispensed through the membrane whereby in use all of the dispensed liquid is consumed prior to the next successive actuation of the delivery means, such that there is avoided any exposure of liquid to ambient air following the dispensing operating period and prior to a next successive actuation of the delivery means.

31. A method of dispensing liquid as an atomized spray comprising the steps of delivering a metered quantity of liquid from a liquid supply means via an outlet valve into contact with a rear face of a perforate membrane with any liquid remaining in said liquid supply means being sealed off by said outlet valve, vibrating the membrane such that liquid is dispensed through the membrane as an atomized spray, and in that the membrane is vibrated for an operating period greater than a dispensing period required for the metered quantity to be fully dispensed such that all of the metered quantity of liquid delivered to the perforate membrane via the outlet valve is consumed to avoid any exposure of liquid to ambient air following the operating period and prior to a next successive delivery of liquid from said liquid supply means to the rear face of the perforate membrane.

\* \* \* \* \*